United States Patent [19]

Bertholet et al.

[11] 4,307,246

[45] Dec. 22, 1981

[54] PROCESS FOR THE PURIFICATION OF ISOLEUCINE

[75] Inventors: Raymond Bertholet, Tour-de-Peilz; Pierre Hirsbrunner, Corseaux, both of Switzerland

[73] Assignee: Societe D'Assistance Technique pour Produits Nestle S.A., Lausanne, Switzerland

[21] Appl. No.: 182,623

[22] Filed: Aug. 29, 1980

[30] Foreign Application Priority Data

Oct. 4, 1979 [CH] Switzerland .......................... 8949/79

[51] Int. Cl.$^3$ .............................................. C07C 99/12
[52] U.S. Cl. .................................................... 562/554
[58] Field of Search ............................... 562/554, 575

[56] References Cited

U.S. PATENT DOCUMENTS 2,471,053  5/1949  Almquist .............................. 562/554
3,960,942  6/1976  Hirsbrunner ........................ 562/554

OTHER PUBLICATIONS

Weissberger, "Technique of Organic Chemistry," vol. III, 2nd Ed., pp. 549–552 (1956).

*Primary Examiner*—G. T. Breitenstein
*Assistant Examiner*—Michael Shippen
*Attorney, Agent, or Firm*—Vogt & O'Donnell

[57] ABSTRACT

From a mixture of isoleucine and leucine in a ratio by weight of at least 3:7, the isoleucine is precipitated in an anhydrous solvent, particularly methyl ethyl ketone, using concentrated sulphuric acid. The precipitate is separated and freed from sulphuric acid, for example by neutralisation with barium hydroxide after elimination of the solvent. Industrial production of marketable isoleucine from a mixture still containing leucine.

7 Claims, No Drawings

PROCESS FOR THE PURIFICATION OF ISOLEUCINE

This invention relates to a process for the purification of isoleucine from a mixture of leucine and isoleucine. In addition to the conventional process for separating leucine and isoleucine, which is based on the difference in solubility of their copper complexes or salts in methanol and of which the yield is very poor, there is also an industrially workable process for enriching isoleucine which is based on the fractional crystallisation of copper salts of leucine and isoleucine at different pH-values in the acid range. However, the purity of the isoleucine obtained by this known process does not exceed 80%.

The process according to the present invention permits isoleucine to be separated even more effectively from leucine and a high degree of purity to be obtained whilst, at the same time, maintaining an industrially favourable yield.

The process according to the invention is characterised in that isoleucine is precipitated in an anhydrous solvent using concentrated sulphuric acid, the precipitate is separated and then freed from sulphuric acid.

It has been found that, firstly, isoleucine and leucine are capable of forming with sulphuric acid two different types of complexes, namely a sulphate of the formula $2AA.H_2SO_4$ and a sesquisulphate of the formula $3AA.2H_2SO_4$ and that, secondly, free sulphuric acid preferentially increases the solubility of leucine sesquisulphate, thus causing the solid phase to be enriched with isoleucine.

The process according to the invention allows a highly pure isoleucine to be obtained in a good yield and in a small number of simple operations from a mixture which is still heavily laden with leucine. Accordingly, the process according to the invention complements industrial processes for extracting amino acids from various animal or vegetable materials during which it is necessary to isolate fractions containing, above all, isoleucine and leucine.

To carry out the process according to the invention, it is possible to extract from fractions of this type a dry mixture which for the most part contains isoleucine and leucine.

It is advisable to use a starting mixture in which the isoleucine and leucine are present in a ratio by weight of at least 30:70. With a lower ratio, the enrichment of the precipitate is too weak even though the yield of isoleucine is excellent. Beyond this ratio, it is possible to obtain strong enrichment for a considerable yield by using a suitable quantity of sulphuric acid. In the context of the invention, the yield of isoleucine is understood to be the quantity of isoleucine which is finally collected in relation to the quantity of isoleucine present in the starting mixture.

The recommended anhydrous solvent is an aliphatic ketone, particularly methyl ethyl ketone. Although acetone for example also gives good results, methyl ethyl ketone is preferable for technical reasons associated with its boiling point and its flash point. For the same reasons, it is preferred to work at ambient temperature, namely at a temperature of the order of 20° C. Temperatures above 30° C. for example give rise to technical difficulties and to an unnecessary increase in costs whereas temperatures below ambient temperature do not produce any improvement in regard to the relation between purity and yield.

The mixture of leucines may be suspended in the solvent in a quantity of from about 5 to 15% by weight, based on the suspension. Below this approximate range, which represents nothing more than a reasonable compromise, the concentration becomes too low for the industrial working of the process to remain viable although both the yield of isoleucine and its purity are better. Beyond this range, yield and purity are inadequate.

In line precisely with the relationship which exists between yield and purity, the quantity of sulphuric acid used is of importance. It may amount to between about 0.5 and 1 times the molar equivalence of the mixture of leucines. With a larger quantity, the leucines are completely dissolved without any precipitate being formed. With a smaller quantity, the sulphuric acid prevents complete dissolution of the leucines and the effect of enrichment of the precipitate obtained is insignificant although the yield is good. Between these limits, the quantity of acid used plays a crucial role. With high values, the yield of crystals is low although the isoleucine content is high. By contrast, with low values, the yields improve but to the detriment of the isoleucine content. In practice, the purifying operation according to the invention may be repeated a certain number of times until the required degree of purity is obtained. To this end, the precipitate may be separated, optionally freed from sulphuric acid and re-introduced into a similar following precipitation stage. The quantity of sulphuric acid to be used in each successive stage is thus preferably selected with great care so as to optimise the process and, in particular, to minimise the number of stages required to reach the required degree of purity without falling below a minimum yield. It is advisable to select this suitable quantity in a range of from 60 to 75% by weight, based on the mixture of leucines involved in each stage.

Thus, from starting mixtures containing isoleucine and leucine in a ratio by weight of from 50:50 to 90:10 for example, it is possible to obtain a 98% pure isoleucine in an isoleucine yield of from 15 to 45% in two to five stages.

It may be pointed out at this juncture that the operation by which the filtrate is freed from sulphuric acid should not present any difficulties to the person skilled in the art. It may be carried out for example by neutralisation with barium hydroxide after elimination of the solvent.

Depending on their respective contents of isoleucine and leucine, the mother liquors from each stage may be recycled to a preceding stage of the same process or may be introduced into a process for the extraction of leucine, for example by way of the hydrochloride.

The present invention is illustrated by the following Examples in which the percentages and ratios quoted are by weight.

EXAMPLE 1

A mixture of isoleucine and leucine in a ratio of 4:1 is obtained by the process described in German Patent No. 24 17 375. 20 g of this mixture are suspended in 400 ml. of methyl ethyl ketone. 14.8 g of 97% $H_2SO_4$ are added, after which the suspension is vigorously stirred for 3 hours at 20° C. The new solid phase formed, which weighs 14 g, is filtered and then dissolved in 200 ml. of water. The resulting solution is neutralised with barium hydroxide and the barium sulphate formed is separated.

The filtrate is concentrated and dried. 9.25 g of an isoleucine still containing 5.8% of leucine are obtained.

This new mixture of amino acids is suspended in 200 ml. of methyl ethyl ketone. 6.4 g of 97% sulphuric acid are then added, followed by vigorous stirring for 3 hours at 20° C. The crystals formed, which weigh 9.5 g, are filtered and then dissolved in 200 ml. of water, followed by neutralisation with Ba(OH)$_2$. After filtration of the BaSO$_4$ and concentration of the filtrate, 6.1 g of L-isoleucine having a purity of 98% are obtained, corresponding to a yield of 38.1%.

EXAMPLE 2

100 g of a mixture containing 50% of leucine and 50% of isoleucine are suspended in 2000 ml. of methyl ethyl ketone. 70 g of 97% H$_2$SO$_4$ are then added, followed by vigorous stirring for 3 hours at a temperature of 25° C. The crystals formed, which weigh 40.5 g, are filtered and suspended in 550 ml. of methyl ethyl ketone. 5.5 g of 97% H$_2$SO$_4$ are then added to the suspension, followed by stirring for 3 hours at 25° C. After filtration, 31.5 g of crystals are obtained.

These crystals are suspended in 500 ml. of methyl ethyl ketone containing 5 g of 97% H$_2$SO$_4$. The resulting suspension is stirred for 3 hours at 25° C. and then filtered, 20.8 g of crystals being obtained.

The crystals obtained are suspended in 250 ml. of methyl ethyl ketone containing 2.5 g of H$_2$SO$_4$. The resulting suspension is stirred for 3 hours at 25° C. and filtered, giving 15.8 g of crystals.

The crystals obtained are suspended in 250 ml. of methyl ethyl ketone containing 2.5 g of 97% H$_2$SO$_4$. The resulting suspension is stirred for 3 hours at 25° C. and filtered. 12.5 g of isoleucine sesquisulphate crystals are obtained and, freed from sulphuric acid using baryta, give 8.25 g of L-isoleucine having a purity of 98.2%. The yield amounts to 16.5%.

We claim:

1. A process for the purification of isoleucine from a mixture of leucine and isoleucine comprising treating said mixture in anhydrous aliphatic ketone with sulphuric acid in a quantity of from about 0.5 to 1 times the molar equivalence of the mixture to form a precipitate, separating the precipitate and freeing the precipitate from sulphuric acid.

2. A process as claimed in claim 1, wherein the anhydrous aliphatic ketone is methyl ethyl ketone.

3. A process as claimed in claim 1, wherein the mixture is suspended in the solvent in a quantity of from about 5 to 15% by weight, based on the suspension.

4. A process as claimed in claim 1, wherein the sulphuric acid is added in a quantity of from 60 to 75% by weight, based on the said mixture.

5. A process as claimed in claim 1, wherein the isoleucine and leucine are present in the starting mixture in a ratio by weight of at least 40:60.

6. A process as claimed in claim 1, wherein the precipitate is subjected to a further precipitation step as recited in claim 1.

7. A process as claimed in claim 6, wherein the precipitate is freed from sulphuric acid prior to being subjected to further precipitation.

* * * * *